(12) United States Patent
Jadhav et al.

(10) Patent No.: US 10,335,229 B2
(45) Date of Patent: *Jul. 2, 2019

(54) VESSEL SEALING INSTRUMENT WITH SUCTION SYSTEM

(71) Applicant: Covidien LP, Mansfield, MA (US)

(72) Inventors: Amarsinh D. Jadhav, Hyderabad (IN); Nikhil P. Mankar, Pune (IN)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/972,168

(22) Filed: May 6, 2018

(65) Prior Publication Data

US 2018/0250069 A1    Sep. 6, 2018

Related U.S. Application Data

(63) Continuation of application No. 14/522,058, filed on Oct. 23, 2014, now Pat. No. 9,974,601.

(60) Provisional application No. 61/906,019, filed on Nov. 19, 2013.

(51) Int. Cl.
| | | |
|---|---|---|
| *A61B 13/00* | (2006.01) | |
| *A61B 18/14* | (2006.01) | |
| *A61B 18/00* | (2006.01) | |

(52) U.S. Cl.
CPC .. *A61B 18/1445* (2013.01); *A61B 2018/0063* (2013.01); *A61B 2018/00404* (2013.01); *A61B 2018/00601* (2013.01); *A61B 2018/146* (2013.01); *A61B 2218/007* (2013.01)

(58) Field of Classification Search
USPC ...................................... 606/37, 51
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |

(Continued)

FOREIGN PATENT DOCUMENTS

| | | |
|---|---|---|
| CN | 201299462 Y | 9/2009 |
| DE | 2415263 A1 | 10/1975 |

(Continued)

OTHER PUBLICATIONS

Levy et al., "Update on Hysterectomy—New Technologies and Techniques" OBG Management, Feb. 2003.

(Continued)

*Primary Examiner* — Nichole F Lavert (57) ABSTRACT

The present disclosure is directed to a forceps having an end effector assembly including first and second jaw members. At least one of the jaw members is movable relative to the other between a spaced-apart position and an approximated position for grasping tissue therebetween. Each jaw member includes an electrically-conductive tissue-contacting surface adapted to connect to a source of energy to treat tissue grasped between the jaw members. A suction system is disposed proximate the first and second jaw members and is configured to apply suction to a surgical site upon activation thereof.

17 Claims, 6 Drawing Sheets

(56) References Cited

U.S. PATENT DOCUMENTS

| | | |
|---|---|---|
| D343,453 S | 1/1994 | Noda |
| D348,930 S | 7/1994 | Olson |
| D349,341 S | 8/1994 | Lichtman et al. |
| 5,336,220 A | 8/1994 | Ryan et al. |
| D354,564 S | 1/1995 | Medema |
| D358,887 S | 5/1995 | Feinberg |
| 5,417,709 A | 5/1995 | Slater |
| 5,554,172 A | 9/1996 | Horner et al. |
| D384,413 S | 9/1997 | Zlock et al. |
| 5,690,660 A | 11/1997 | Kauker et al. |
| H1745 H | 8/1998 | Paraschac |
| D402,028 S | 12/1998 | Grimm et al. |
| D408,018 S | 4/1999 | McNaughton |
| 5,938,589 A | 8/1999 | Wako et al. |
| D416,089 S | 11/1999 | Barton et al. |
| D424,694 S | 5/2000 | Tetzlaff et al. |
| D425,201 S | 5/2000 | Tetzlaff et al. |
| 6,056,735 A | 5/2000 | Okada et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,740,079 B1 | 5/2004 | Eggers et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,112,199 B2 | 9/2006 | Cosmescu |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,998,095 B2 | 8/2011 | McAuley |
| D649,249 S | 11/2011 | Guerra |
| D649,643 S | 11/2011 | Allen, IV et al. |
| 8,075,580 B2 | 12/2011 | Makower |
| 8,142,425 B2 | 3/2012 | Eggers |
| D661,394 S | 6/2012 | Romero et al. |
| 8,207,651 B2 | 6/2012 | Gilbert |
| D670,808 S | 11/2012 | Moua et al. |
| 8,303,581 B2 | 11/2012 | Arts et al. |
| D680,220 S | 4/2013 | Rachlin |
| 8,469,957 B2 | 6/2013 | Roy |
| 8,562,598 B2 | 10/2013 | Falkenstein et al. |
| 8,641,713 B2 | 2/2014 | Johnson et al. |
| 9,974,601 B2 | 5/2018 | Jadhav et al. |
| 2005/0165427 A1 | 7/2005 | Jahns et al. |
| 2006/0253126 A1 | 11/2006 | Bjerken et al. |
| 2006/0271030 A1 | 11/2006 | Francis et al. |
| 2009/0177094 A1 | 7/2009 | Brown |
| 2009/0299364 A1 | 12/2009 | Batchelor et al. |
| 2012/0116379 A1* | 5/2012 | Yates ............... A61B 17/00234 606/33 |
| 2012/0184990 A1* | 7/2012 | Twomey ............ A61B 17/2909 606/206 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 B4 | 3/1999 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009318 U1 | 8/2007 |
| DE | 202007009317 U1 | 10/2007 |
| DE | 10031773 B4 | 11/2007 |
| DE | 202007016233 U1 | 1/2008 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61501068 | 9/1984 |
| JP | 1147150 A | 6/1989 |
| JP | 6502328 | 3/1992 |
| JP | 55106 | 1/1993 |
| JP | 0540112 | 2/1993 |
| JP | 0006030945 A | 2/1994 |
| JP | 6121797 A | 5/1994 |
| JP | 6285078 A | 10/1994 |
| JP | 06343644 A | 12/1994 |
| JP | 6511401 | 12/1994 |
| JP | 07265328 A | 10/1995 |
| JP | H0856955 | 5/1996 |
| JP | 08252263 A1 | 10/1996 |
| JP | 8289895 A | 11/1996 |
| JP | 8317934 A | 12/1996 |
| JP | 8317936 A | 12/1996 |
| JP | 09000538 A | 1/1997 |
| JP | H0910223 A | 1/1997 |
| JP | 9122138 A | 5/1997 |
| JP | 0010000195 A | 1/1998 |
| JP | H1024051 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | 11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 A | 1/2001 |
| JP | 2001029355 | 2/2001 |
| JP | 2001029356 A | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |

(56) References Cited

FOREIGN PATENT DOCUMENTS

| | | |
|---|---|---|
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 2005110264 A3 | 4/2006 |
| WO | 2008040483 A1 | 4/2008 |
| WO | 2011018154 A1 | 2/2011 |

OTHER PUBLICATIONS

Barbara Levy, "Use of a New Vessel Ligation Device During Vaginal Hysterectomy"; FIGO 2000, Washington, D.C.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001 (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.

(56) References Cited

OTHER PUBLICATIONS

McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
"Electrosurgery: A Historical Overview", Innovations in Electrosurgery; Sales/Product Literature; Dec. 31, 2000.
Heniford et al. "Initial Research and Clinical Results with an Electrothermal Bipolar Vessel Sealer" Oct. 1999.
Heniford et al. "Initial Results with an Electrothermal Bipolar Vessel Sealer"; Surgical Endoscopy (2000) 15:799-801.
"Reducing Needlestick Injuries in the Operating Room"; Sales/Product Literature 2001.

* cited by examiner

VESSEL SEALING INSTRUMENT WITH SUCTION SYSTEM

CROSS REFERENCE TO RELATED APPLICATIONS

The present application is a continuation of U.S. patent application Ser. No. 14/522,058, filed Oct. 23, 2014, now U.S. Pat. No. 9,974,601 which claims the benefit of and priority to U.S. Provisional Patent Application Ser. No. 61/906,019, filed Nov. 19, 2013. The entire contents of each of the above applications are hereby incorporated by reference.

BACKGROUND

1. Technical Field

The present disclosure relates to the use of medical instruments. More particularly, the present disclosure is directed to vessel sealing devices.

2. Background of the Related Art

A surgical forceps is a plier-like instrument which relies on mechanical action between its jaw members to grasp, clamp, and constrict tissue. Energy-based surgical forceps utilize both mechanical clamping action and energy, e.g., RF energy, ultrasonic energy, microwave energy, thermal energy, light energy, etc., to affect hemostasis by heating tissue and blood vessels to coagulate and/or cauterize tissue. Certain surgical procedures require more than simply coagulating/cauterizing tissue and rely on the unique combination of clamping pressure, precise energy control, and gap distance (i.e., the distance between opposing jaw members when closed about tissue) to "seal" tissue.

Typically, once tissue is treated, e.g., sealed, the surgeon has to accurately sever the tissue along the newly formed tissue seal. Accordingly, many surgical forceps have been designed which incorporate a knife or blade member that effectively severs the tissue after forming a tissue seal.

Vessel sealing instruments are used in many surgical procedures to seal and dissect tissue. Occasionally, during a surgical procedure, bleeding will occur while the surgeon is using the vessel sealing instrument. In such situations, the surgeon may be required to stop use of the vessel sealing instrument, remove it from the surgical site, and insert a separate suction device in order to clear the blood and other bodily fluids that have collected at the surgical site.

SUMMARY

As shown in the drawings and described throughout the following description, as is traditional when referring to relative positioning on a surgical instrument, the term "proximal" refers to the end of the apparatus that is closer to the user and the term "distal" refers to the end of the apparatus that is farther away from the user. The term "clinician" refers to any medical professional (e.g., doctor, surgeon, nurse, or the like) performing a medical procedure involving the use of embodiments described herein.

In at least one aspect of the present disclosure, a forceps is provided that includes an end effector assembly having first and second jaw members attached at a distal end of a shaft. At least one of the jaw members is movable relative to the other between a spaced-apart position and an approximated position for grasping tissue therebetween. Each jaw member includes an electrically-conductive tissue-contacting surface adapted to connect to a source of energy to treat tissue grasped between the jaw members A suction system is disposed proximate the first and second jaw members and is configured to apply suction to a surgical site upon activation thereof.

In another aspect of the present disclosure, the suction system includes a tube attached to the shaft and is configured to connect to a low-pressure source. The tube may be disposed within the shaft and may be selectively slidable within the shaft from a retracted position to a deployed position. In the deployed position, at least a portion of the tube may be extended to a position distal to the jaw members.

In another aspect of the present disclosure, one of the first or second jaw members is fixed and integral with the shaft. The tube may be offset relative to the fixed jaw member.

In another aspect of the present disclosure, the forceps includes a blade disposed within the shaft and configured to cut tissue disposed between the jaw members. An actuator is configured to selectively deploy and retract the tube.

Another aspect of the present disclosure relates to a method for performing a surgical procedure including providing a vessel sealing device having two opposable jaw members operably connected to a shaft. At least one of the jaw members is configured to move relative to the other between an open position and a clamped position. A suction system is included proximate one or both of the jaw members.

The method also includes: grasping a vessel between the two jaw members and applying electrosurgical energy to seal tissue; and activating the suction system to remove bodily fluids from the surgical site during the surgical procedure.

The suction system may include a suction tube slidably disposed within the shaft of the vessel sealing device and the method may include the step of deploying the suction tube from a retracted position to a deployed position to remove fluid and debris from the surgical site upon activation of the suction system.

The method may include the steps of providing a vessel sealing device having two opposable jaw members operably connected to a shaft, where at least one of the jaw members is configured to move relative to the other between an open position and a clamped position, disposing a suction system proximate the first and second jaw members that is configured to apply suction to a surgical site upon activation thereof, grasping a vessel between the two jaw members, applying electrosurgical energy to seal tissue, and suctioning bodily fluids from a surgical site during the surgical procedure.

In another aspect of the present disclosure, a vessel sealing device includes an end effector assembly having first and second jaw members, at least one of the jaw members being movable relative to the other between a spaced-apart position and an approximated position for grasping tissue therebetween. Each jaw member includes an electrically-conductive tissue-contacting surface adapted to connect to a source of energy to treat tissue grasped between the jaw members. A suction system is disposed proximate the first and second jaw members and is configured to apply suction to a surgical site upon activation thereof. The suction system includes a tube slidably disposed on or in the shaft radially outwardly of the second jaw member relative to a longitudinal axis of the shaft. The tube is configured to move between a retracted position wherein the tube is proximal of a distal end of the first and second jaw members to a deployed position wherein at least a portion of the tube extends distally relative to the distal end of the first and second jaw members.

The tube may be disposed within the shaft. The tube may also be connected to a suction tube deployment device that is operably connected to the housing. The suction tube deployment device may include an actuator that deploys the tube from the retracted position via a button, a handle, a mechanical deployment system, an electro-mechanical deployment system, a lever, or a slide.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

Figure 1A:
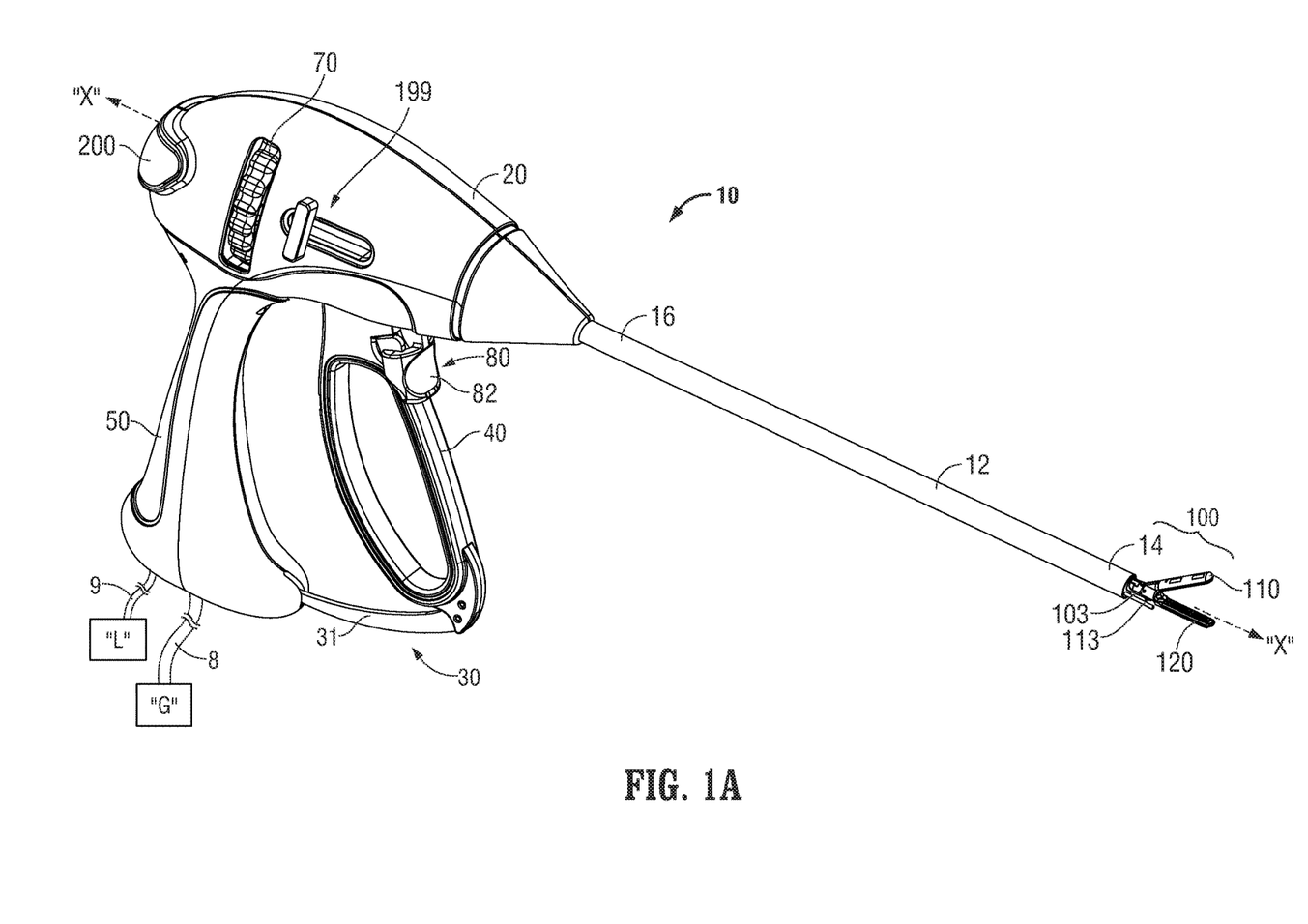
FIG. 1A is a perspective view of an embodiment of a medical device in accordance with one embodiment of the present disclosure.
Figure 2:
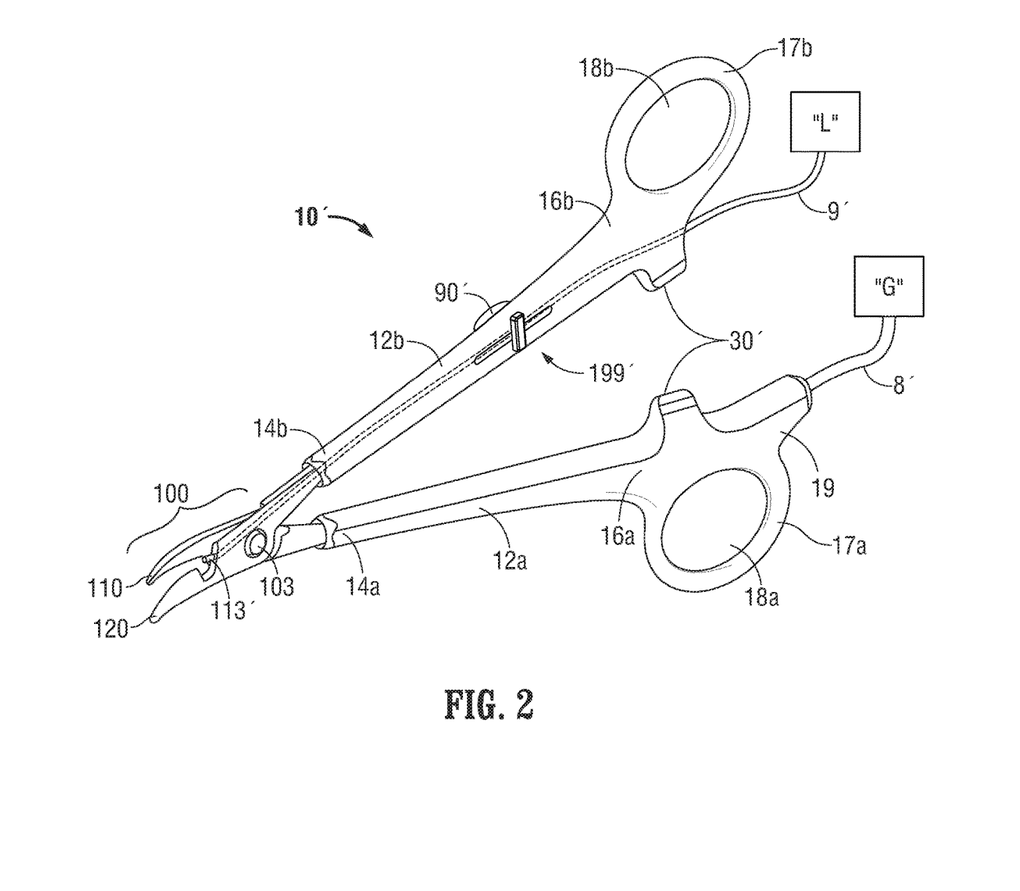
FIG. 2 is a perspective view of an open medical device in accordance with another embodiment the present disclosure.

Referring now to FIGS. 1A and 2, FIG. 1A depicts a forceps 10 for use in connection with endoscopic surgical procedures and FIG. 2 depicts an open forceps 10' contemplated for use in connection with traditional open surgical procedures. For the purposes herein, either an endoscopic device, e.g., forceps 10, an open device, e.g., forceps 10', or any other suitable surgical device may be utilized in accordance with the present disclosure. Different electrical and mechanical connections and considerations may apply to each particular type of device, however, the aspects and features of the present disclosure remain generally consistent regardless of the particular device used.

Turning now to FIG. 1A, an endoscopic forceps 10 is shown including a housing 20 having a shaft 12 that extends therefrom and defines a longitudinal axis "X-X" therethrough, a handle assembly 30, and an end effector assembly 100. Additionally, forceps 10 may be configured to include a rotating assembly 70 and a trigger assembly 80, as shown in FIG. 1.

Forceps 10 further includes a shaft 12 having a distal end 14 configured to mechanically engage end effector assembly 100 and a proximal end 16 that mechanically engages housing 20. Forceps 10 also includes cable 8 that connects forceps 10 to an energy source, e.g., a generator "G", or other suitable power source, although forceps 10 may alternatively be configured as a battery-powered device. Cable 8 includes a wire or wires (not shown) extending therethrough that has sufficient length to extend through shaft 12 in order to provide energy to at least one of tissue-contacting surfaces 112, 122 (FIG. 1F) of jaw members 110, 120, respectively. An activation switch 200 may be provided on housing 20 for selectively supplying energy to jaw members 110, 120.

With continued reference to FIG. 1A, handle assembly 30 includes fixed handle 50 and a moveable handle 40. Fixed handle 50 is integrally associated with or rigidly attached to housing 20 and handle 40 is moveable relative to fixed handle 50.

Moveable handle 40 is ultimately connected to a drive assembly (not shown in FIG. 1A) that, together, mechanically cooperate to impart movement of jaw members 110 and 120 between a spaced-apart position and an approximated position to grasp tissue disposed between jaw members 110, 120. As shown in FIG. 1A, moveable handle 40 is initially spaced-apart from fixed handle 50 and, correspondingly, jaw members 110, 120 are disposed in the spaced-apart position. Moveable handle 40 is compressible from this initial position to a compressed position corresponding to the approximated position of jaw members 110, 120.

Rotating assembly 70 is rotatable in either direction about longitudinal axis "X-X" to rotate end effector assembly 100 about longitudinal axis "X-X." Housing 20 houses the internal working components of forceps 10.

Forceps 10 may also include a ratchet assembly 31 for selectively locking the jaw members 110 and 120 relative to one another at various positions during pivoting. Ratchet assembly 31 may include graduations or other visual markings that enable the user to easily and quickly ascertain and control the amount of closure force desired between the jaw members 110 and 120.

In order to effectively "seal" tissue or vessels, two predominant mechanical parameters should be accurately controlled: 1) the pressure or closure force applied to the vessel or tissue; and 2) the gap distance between the conductive tissue contacting surfaces (electrodes).

Tissue pressures within a working range of about 3 kg/cm2 to about 16 kg/cm2 and, advantageously, within a working range of 7 kg/cm2 to 13 kg/cm2 have been shown to be effective for sealing arteries and vascular bundles.

In some embodiments, one of the jaw members, e.g., 120, includes at least one stop member 175 (see FIG. 1F) disposed on the inner facing surface of the electrically conductive sealing surface 122 (and/or 112). The stop member(s) is designed to facilitate gripping and manipulation of tissue and to define a gap "g" between opposing jaw members 110 and 120 during sealing (See FIG. 3A). In some embodiments, the separation distance during sealing or the gap distance "g" is within the range of about 0.001 inches (about 0.03 millimeters) to about 0.006 inches (about 0.016 millimeters).

Figure 1B:
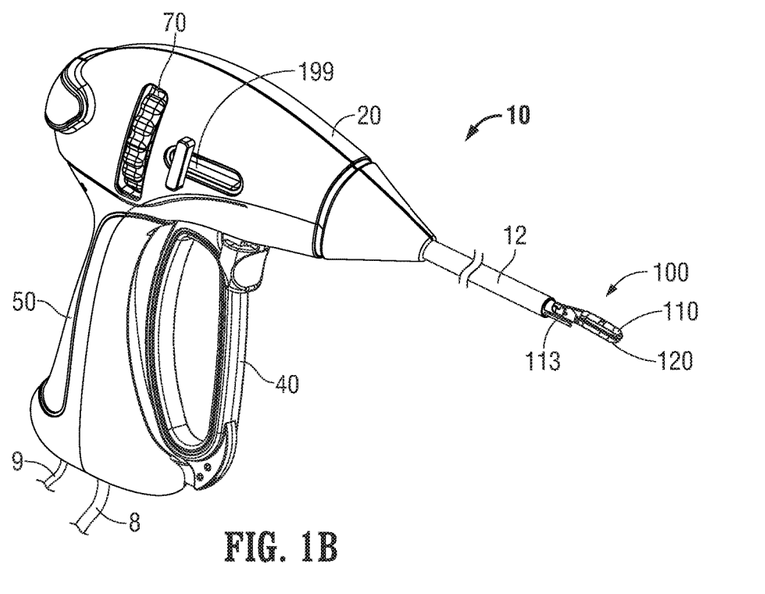
FIG. 1B is a partial, perspective view of the embodiment of FIG. 1, shown with the jaw members in a closed position and a suction tube in a retracted position.
Figure 1C:
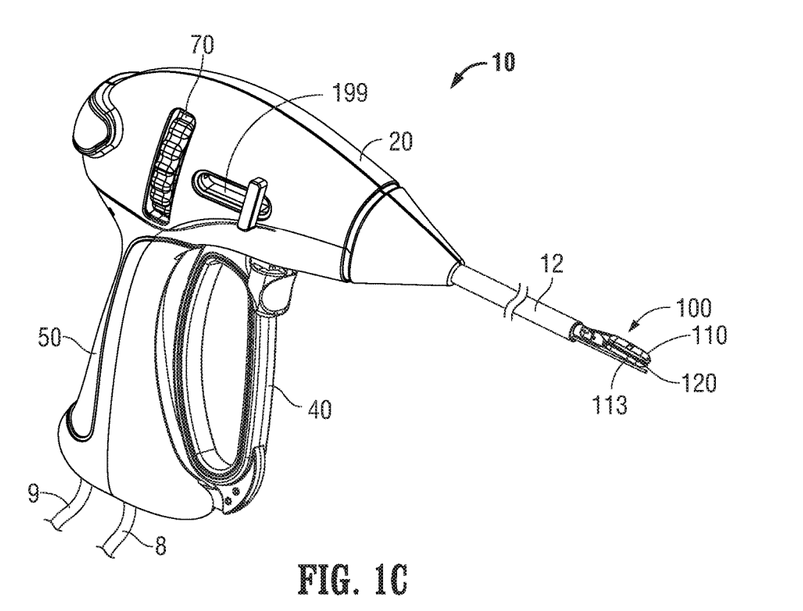
FIG. 1C is a partial, perspective view of the embodiment of FIG. 1, shown with the jaw members in a closed position and a suction tube in a deployed position.
Figure 1D:
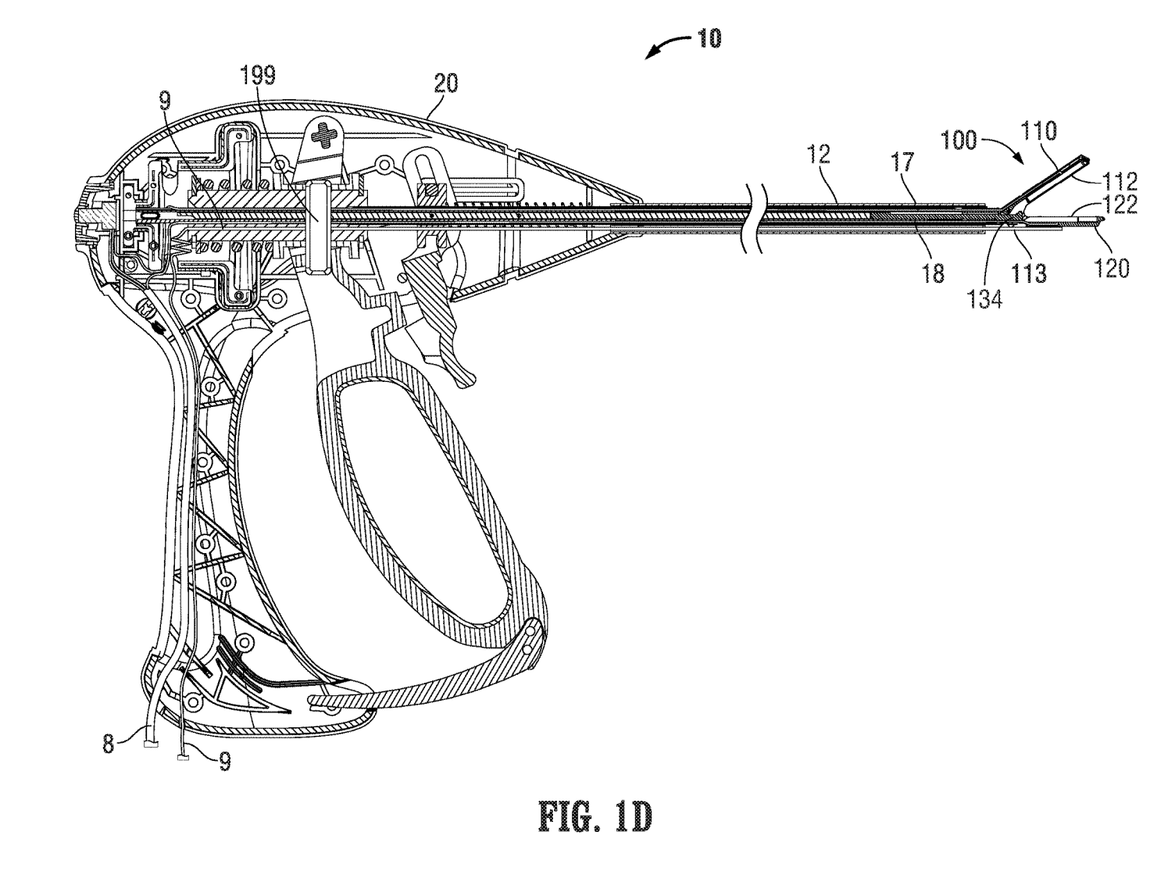
FIG. 1D is a partial, cross-sectional, side view of an embodiment of the medical device in accordance with the present disclosure, shown with the jaw members in an open position and the suction tube in a partially retracted position.
Figure 1E:
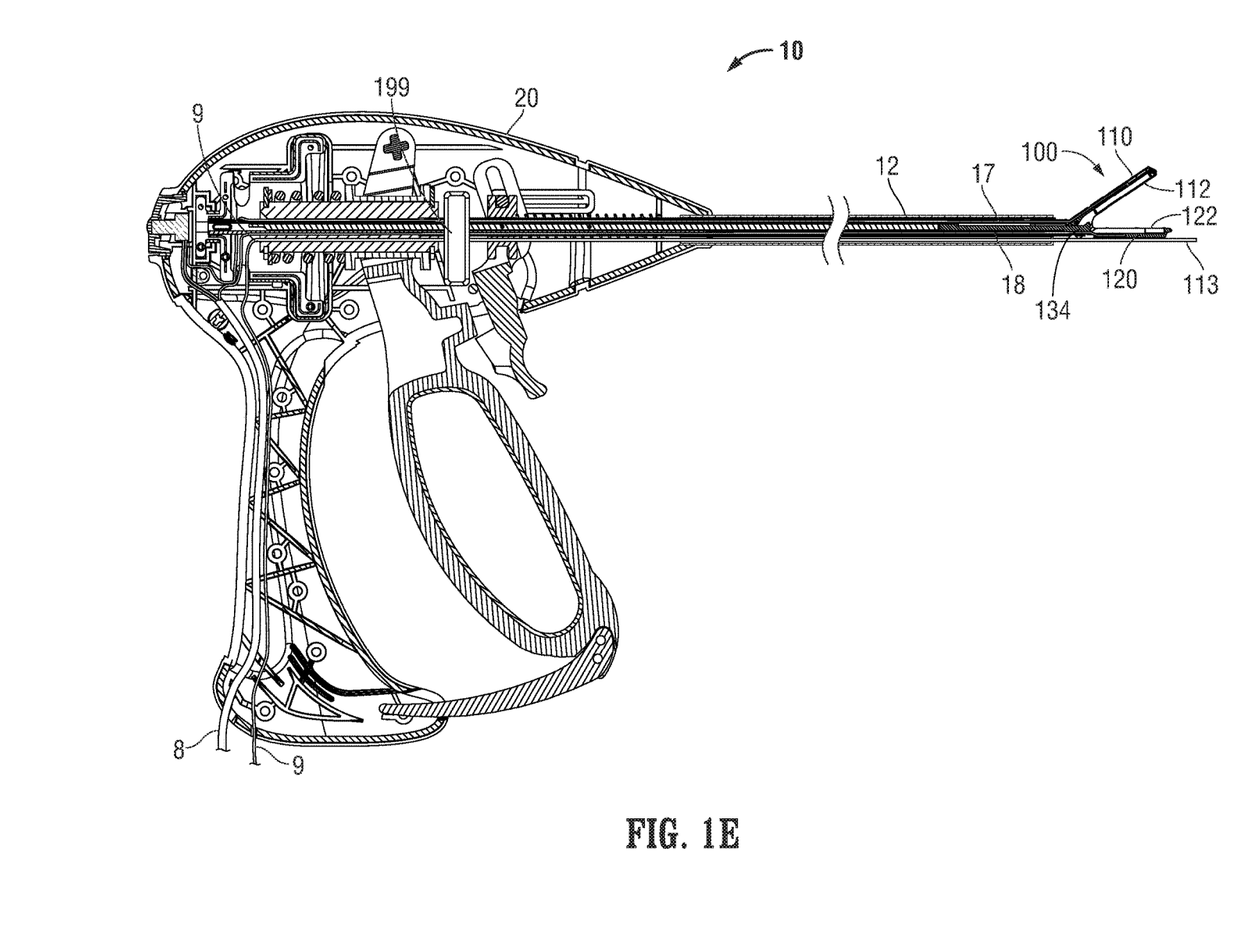
FIG. 1E is a partial, cross-sectional, side view of an embodiment of the medical device of FIG. 1D, shown with the jaw members in an open position and a suction tube in a fully deployed position.
Figure 1F:
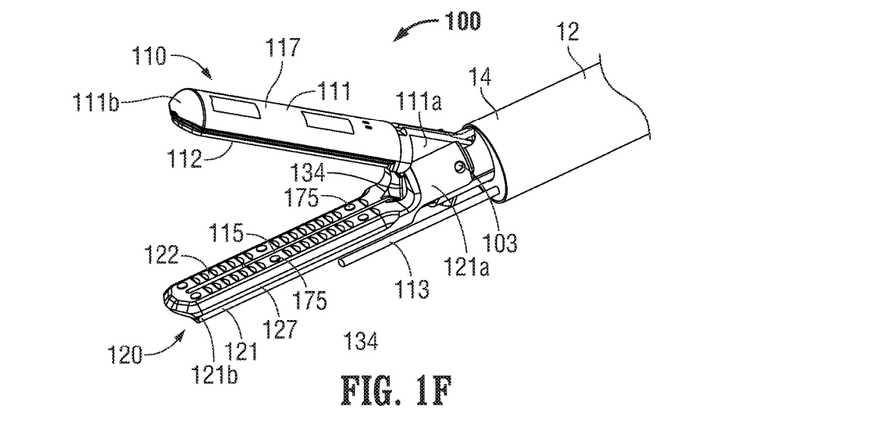
FIG. 1F is an enlarged, perspective view of the jaw members shown in an open position with the suction tube in a partially deployed position in accordance with the present disclosure.

With reference to FIG. 1F, end effector assembly 100 of forceps 10 (FIG. 1A) is shown. End effector assembly 100 may similarly be used in conjunction with forceps 10' (FIG. 2), or any other suitable surgical device. For purposes of simplicity, end effector assembly 100 is described herein as configured for use with forceps 10 (FIG. 1).

Each jaw member 110, 120 of end effector assembly 100 includes a proximal flange portion 111a, 121a, a distal jaw portion 111b, 121b, an outer insulative jaw housing 117, 127 and a tissue-contacting plate 112, 122, respectively. Proximal flange portions 111a, 121a of jaw members 110, 120 are pivotably coupled to one another about a pivot 103 for moving jaw members 110, 120 between the spaced-apart and approximated positions. Distal jaw portions 111b, 121b of jaw members 110, 120 are configured to support jaw housings 117, 127, and tissue-contacting plates 114, 124, respectively, thereon. Further, one of the jaw members, e.g., jaw member 120, may include an energy-based cutting member (not shown) disposed thereon, or a channel 115 for allowing a mechanical cutting member (not shown), e.g., a knife assembly as described above, to pass therethrough. Trigger 82 of trigger assembly 80 is operably coupled to the knife assembly (shown in FIGS. 1D-1F) for selectively translating a knife blade 134 (FIGS. 1D-1F and 3A-3B) through a knife channel 115 (FIG. 1F) defined within one or both of jaw members 110, 120 to cut tissue disposed between jaw members 110, 120. The knife assembly (shown in FIGS. 1D-1F) is configured for longitudinal translation through channel 115 of jaw members 110, 120, e.g., upon activation of a trigger 82 operably coupled to the knife assembly (shown in FIGS. 1D-1F), to mechanically cut tissue grasped between jaw members 110, 120. Knife assembly (shown in FIGS. 1D-1F) may be configured for mechanical cutting, or may be energizable, e.g., via electrical coupling to generator "G" (FIG. 1A) via the one or more wires (not shown) of cable 8 (FIG. 1A), for electro-mechanically cutting tissue.

In embodiments having an electrical cutting member, the electrical cutting member can be similarly coupled to trigger 82 (FIG. 1A) and generator "G" (FIG. 1A) such that energy, e.g., electrosurgical energy, may be selectively supplied to cutting member and conducted through tissue disposed between jaw members 110, 120 to either or both of tissue-contacting plates 112, 122 to cut tissue in a second mode of operation. A first insulating member may surround electrical cutting member to insulate tissue-contacting plate 122 and electrical cutting member from one another. A second insulating member (not shown) may be disposed within a longitudinal slot defined within tissue-contacting plate 112 of jaw member 110 that opposes electrical cutting member to insulate electrical cutting member from tissue-contacting plate 112 of jaw member 110 when jaw members 110, 120 are disposed in the approximated position.

Tissue-contacting plates 112, 122 are formed from an electrically conductive material for conducting electrical energy therebetween for treating tissue, although tissue-contacting plates 112, 122 may alternatively be configured to conduct any suitable energy through tissue grasped therebetween for energy-based tissue treatment, e.g., tissue sealing. In embodiments having an energy-based cutting member (not shown), the energy-based cutting member may be formed from an electrically conductive material for conducting electrical energy between energy-based cutting member and one or both of tissue-contacting plates 112, 122 for electrically cutting tissue. Energy-based cutting member may alternatively be configured to conduct any suitable energy through tissue for electrically cutting tissue.

Tissue-contacting plates 112, 122 are coupled to an activation switch such as trigger 82 (FIG. 1A) and generator "G" (FIG. 1A) or other suitable source of energy, e.g., via the wires (not shown) extending from cable 8 (FIG. 1A) through forceps 10, such that energy, e.g., electrosurgical energy, may be selectively supplied to tissue-contacting plate 112 and/or tissue-contacting plate 122 and conducted therebetween and through tissue disposed between jaw members 110, 120 to treat, e.g., seal, tissue in a first mode of operation. In embodiments where the electrical or mechanical cutting mechanisms and the tissue contacting plates are both activated via trigger 82, tissue may be simultaneously sealed and cut.

Referring now to FIGS. 1A-1F, a suction system is configured for use with forceps 10 (FIG. 1A). The suction system as described herein may also be configured for use with open forceps 10' as shown in FIG. 2. However, for purposes of brevity, the suction system will be described in detail herein configured for use with forceps 10 (FIG. 1A).

As shown, the suction system includes one or more tubes 113 connected to a low pressure source "L" via piping 9. Low pressure source "L" may be any device capable of providing a suction flow in tube 113, such as, but not limited to, a vacuum pump. The tube 113 may be contained within shaft 12 as shown in FIGS. 1A-1F, or may alternatively be attached externally to shaft 12. Tube 113 may also be used for irrigation by connecting tube 113 to a source of fluid such as, but not limited to, saline solution. In this instance the suction system may be designed for positive or negative flow.

In some embodiments, tube 113 may be disposed on or within forceps 10 in a fixed manner such that tube 113 may not slide longitudinally and is thus positioned at a fixed extension from shaft 12. However, as shown, tube 113 is slidably disposed within the forceps 10 and is selectively extendable via an actuator 199 such that movement of the actuator 199 from an un-actuated position to an actuated position causes tube 113 to translate between a retracted position and a deployed position. Actuator 199 may include one or more buttons, a handle, a mechanical deployment system, an electro-mechanical deployment system, a lever, or a slide, all configured to move the tube between the retracted and deployed position.

At least part of the tube 113 is offset relative to or disposed proximate the first and second jaw 110, 120 members and is configured to apply suction to the area proximate the first and second jaw members 110, 120. Tube 113 may be disposed underneath/above (radially offset) relative to one or both of the jaw members 110, 120. Alternatively, tube 113 may be disposed in any other suitable manner, such as, but not limited to, within a jaw member 120.

As shown in FIG. 1B, the tube 113 is shown in a retracted position such that the tube 113 does not extend past the grasping range of the jaw members but still partially extends from shaft 12. Tube 113 may also be fully enclosed by the shaft 12 when in the retracted position. FIG. 1D shows the tube 113 partially extended below jaw member 120. In some embodiments, a locking mechanism (not shown) may be included to hold the tube 113 in the retracted position until a user unlocks the tube 113 for selective movement in order to prevent accidental deployment of tube 113. The locking mechanism may be automatically activated (such as by a spring-loaded latch) or manually activated (such as by a finger switch or knob) upon transitioning the tube 113 to the retracted position.

FIGS. 1C and 1E show tube 113 in a fully deployed position extending at least partially beyond end effector 100. In some embodiments, the fully deployed position of the tube 113 may not extend beyond the end effector 100. In some embodiments, a locking mechanism may be included to hold the tube 113 in the deployed position until a user unlocks the tube 113 for selective movement in order to prevent accidental retraction of tube 113 during a procedure. The locking mechanism may be automatically activated (such as by a spring-loaded latch) or manually activated (such as by a finger switch or knob) upon the tube 113 reaching the deployed position.

A suction valve, suction activator, or the like (not shown) may be included on or integrated with the housing 20 such that activation of a suction flow through tube 113 may be easily effected by a user by using, e.g., a handswitch. In some embodiments, the suction activator may be separate from the housing 20, such as a footswitch. In some embodiments, the actuator 199, as described above, also acts as a suction valve or the like such that when the actuator 199 is moved from the un-actuated position (FIG. 1B) to the actuated position (FIG. 1C), the actuator simultaneously activates suction flow through tube 113. The suction flow may begin when the actuator 199 reaches the fully actuated position (FIG. 1C), or at some predetermined position prior to the fully actuated position. In some embodiments, the user may be required to hold the actuator 199 in the actuated position (FIG. 1C) for a preset time period to begin suction. In other embodiments, a button or contact (not shown) may be disposed at the end of the path of movement of actuator 199 such that when actuator 199 is moved to the actuated position (FIG. 1C), the button or electrical contact initiates suction.

While the actuator 199 is shown to operate in a parallel linear fashion along with tube 113, the actuator 199 may be configured in any desired mechanical format to accommodate a desired ergonomic instrument layout to facilitate activation.

Referring now to the embodiment of FIG. 2, open forceps 10' is shown including two elongated shafts 12a and 12b, each having a proximal end 16a and 16b, and a distal end 14a and 14b, respectively. Similar to forceps 10 (FIG. 1A), forceps 10' is configured for use with end effector assembly 100. More specifically, end effector assembly 100 is attached to distal ends 14a and 14b of shafts 12a and 12b, respectively. As mentioned above, end effector assembly 100 includes a pair of opposing jaw members 110 and 120 that are pivotably connected about pivot 103. Each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 12a and 12b relative to one another which, in turn, pivots jaw members 110 and 120 from an open position, wherein the jaw members 110 and 120 are disposed in spaced-apart relation relative to one another, to a closed position, wherein the jaw members 110 and 120 cooperate to grasp tissue therebetween.

A ratchet assembly 30' may be included for selectively locking the jaw members 110 and 120 relative to one another at various positions during pivoting. Ratchet assembly 30' may include graduations or other visual markings that enable the user to easily and quickly ascertain and control the amount of closure force desired between the jaw members 110 and 120.

With continued reference to FIG. 2, one of the shafts, e.g., shaft 12a, includes a proximal shaft connector 19 which is designed to connect the forceps 10' to a source of energy, e.g., generator "G". Proximal shaft connector 19 secures an electrosurgical cable 8' to forceps 10' such that the user may selectively apply energy to jaw members 110 and 120, as needed. One of the shafts, e.g., shaft 12a, includes an activation switch 90' for selectively supplying energy to jaw members 110, 120.

Forceps 10' includes a suction system disposed proximate the first and second jaw members and configured to apply suction to an area proximate the first and second jaw members. The suction system includes a tube 113', similar to tube 113 as described above, that is connected to a suction source "L" as described herein. Tube 113' may be slidably disposed within at least one of the shaft members 12a, 12b and selectively extendable from an opening defined proximally of the end effector 100. Tube 113' may also be connected to an actuator 199', similar to actuator 199 as described above, such that movement of actuator 199' between an un-actuated position and an actuated position causes movement of tube 113' between the retracted position and the deployed position.

Further disclosed is a method for performing a surgical procedure including the steps of providing a vessel sealing device such as forceps 10, open forceps 10', or other medical instrument having two opposable jaw members operably connected to a shaft, at least one of the jaw members configured to move relative to the other between an open position and a clamped position A suction system is included proximate one or both of the jaw members.

Figure 3A:
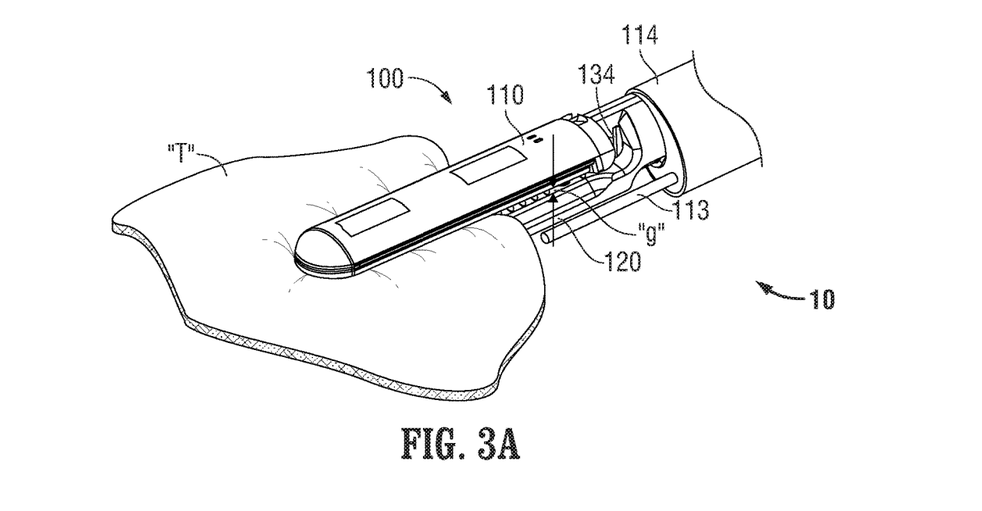
FIG. 3A is an enlarged, perspective view of the jaw members shown engaging tissue with the suction tube in a retracted position.
Figure 3B:
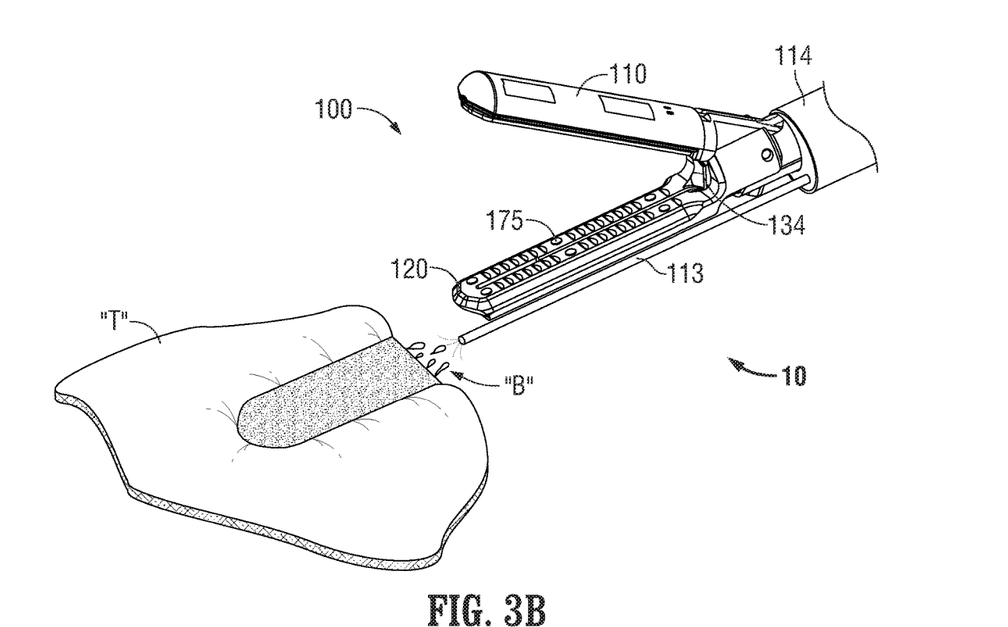
FIG. 3B is an enlarged, perspective view of the jaw members shown disengaged from tissue and with the suction tube in a deployed position.

Referring now to FIGS. 3A and 3B, the method further includes the step of grasping a vessel or tissue "T" between the two jaw members and applying electrosurgical energy to seal tissue "T". Before or after sealing, bodily fluids "B" may form at the surgical site. To remove the bodily fluids "B", the user activates the suction system to remove bodily fluids "B" from the surgical site (FIG. 3B).

As described herein, the tube 113 may be slidably disposed in forceps 10, and the method may also include the step of deploying the tube 113 from the retracted position to the deployed position to remove fluid and debris from the surgical site. The method may also include the step of retracting the tube 113 after use.

The various embodiments disclosed herein may also be configured to work with robotic surgical systems and what is commonly referred to as "Telesurgery". Such systems employ various robotic elements to assist the surgeon in the operating room and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of the herein described forceps (e.g., end effectors, suction systems, knifes, etc.) which may complement the use of one or more of the embodiments described herein. The movement of the master handles may be scaled so that the working ends have a corresponding movement that is different, smaller, or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, suction strength/pressure drop, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The embodiments described with reference to the attached drawings are presented only to demonstrate certain examples of the disclosure. Other elements, steps, methods, and techniques that are insubstantially different from those described above and/or in the appended claims are also intended to be within the scope of the disclosure.

What is claimed is:

1. A forceps, comprising:
a first elongated shaft having a first proximal portion and a first distal portion;
a second elongated shaft having a second proximal portion and a second distal portion;
a first jaw member secured to and extending from the first distal portion;
a second jaw member secured to and extending from the second distal portion, the first and second jaw members moveable about a pivot between an open position in which the first and second jaw members are spaced-apart from one another and a closed position in which the first and second jaw members cooperate to grasp tissue therebetween; and
a tube extending from the first proximal portion to the first distal portion and including a distal tube segment, the distal tube segment slidable relative to the first and second jaw members between a retracted position relative to the first and second jaw members and a deployed position relative to the first and second jaw members distal of the retracted position.

2. The forceps according to claim 1, wherein the tube is configured to apply suction proximate the first and second jaw members.

3. The forceps according to claim 1, wherein the tube is configured to apply irrigation proximate the first and second jaw members.

4. The forceps according to claim 1, wherein a segment of the tube is disposed within the first elongated shaft.

5. The forceps according to claim 1, further comprising an actuator disposed on the first elongated shaft and operably coupled to the tube, the actuator slidable from an unactuated position to an actuated position to slide the distal tube segment from the retracted position to the deployed position.

6. The forceps according to claim 1, wherein in the deployed position, the distal tube segment is distal of the first and second jaw members.

7. The forceps according to claim 1, wherein each of the first and second jaw members includes an electrically-conductive tissue-contacting surface adapted to connect to a source of energy to treat tissue grasped between the first and second jaw members.

8. A forceps, comprising:
a first shaft having a distal portion;
an end effector assembly supported on the distal portion of the first shaft and including first and second jaw members pivotable relative to one another between a spaced-apart position and an approximated position for grasping tissue therebetween;
a tube extending along the distal portion of the first shaft and including a distal tube segment, the distal tube segment slidable relative to the first and second jaw members between a retracted position relative to the first and second jaw members and a deployed position relative to the first and second jaw members distal of the retracted position.

9. The forceps according to claim 8, wherein the tube is configured to apply suction proximate the first and second jaw members.

10. The forceps according to claim 8, further comprising a first handle secured to a proximal portion of the first shaft and a second handle secured to a proximal portion of a second shaft, wherein the first jaw member is secured to the distal portion of the first shaft and the second jaw member secured to a distal portion of the second shaft, the first and second handles movable towards and away from one another to pivot the first and second jaw members between the spaced-apart and approximated positions.

11. The forceps according to claim 10, wherein the tube is connected to a suction tube deployment device that is operably connected to the first handle.

12. The forceps according to claim 8, further comprising a housing having a fixed handle and a movable handle, the first shaft extending from the housing, the moveable handle movable towards the fixed handle to pivot the first and second jaw members towards the approximated position.

13. The forceps according to claim 12, wherein the first shaft defines a longitudinal axis of the forceps that passes between the first and second jaw members.

14. The forceps according to claim 12, wherein the tube is connected to a suction tube deployment device that is operably connected to the housing.

15. The forceps according to claim 8, wherein each of the first and second jaw members includes an electrically-conductive tissue-contacting surface adapted to connect to a source of energy to treat tissue grasped between the first and second jaw members.

16. The forceps according to claim 8, wherein a segment of the tube is disposed within the first shaft.

17. The forceps according to claim 8, further comprising an actuator configured to slide the distal tube segment between the retracted position and the deployed position via at least one of a button, a handle, a mechanical deployment system, an electro-mechanical deployment system, a lever, or a slide.

\* \* \* \* \*